United States Patent [19]

Wallstén

[11] Patent Number: 5,571,153
[45] Date of Patent: Nov. 5, 1996

[54] DEVICE FOR HYPERTHERMIA TREATMENT

[76] Inventor: Hans I. Wallstén, Villa Pré-Boisé, CH-1141 Denens, Switzerland

[21] Appl. No.: 616,042

[22] Filed: Mar. 25, 1996

Related U.S. Application Data

[63] Continuation of Ser. No. 204,358, Mar. 29, 1994, abandoned.

[30] Foreign Application Priority Data

Sep. 20, 1991 [CH] Switzerland ............................ 910728
Apr. 16, 1992 [CH] Switzerland ............................ 920224

[51] Int. Cl.$^6$ .................................................... A61B 17/36
[52] U.S. Cl. ............................... 607/98; 606/27; 606/28; 606/31; 604/114
[58] Field of Search .......................... 604/96, 113, 114; 606/28, 31, 33; 607/98, 99, 104, 116, 138, 96, 105, 113

[56] References Cited

U.S. PATENT DOCUMENTS

| | | |
|---|---|---|
| 1,786,373 | 12/1930 | Walker . |
| 1,951,904 | 3/1934 | Garshells . |
| 2,043,083 | 6/1936 | Wappler . |
| 2,074,634 | 3/1937 | Ackermann . |
| 2,077,453 | 4/1937 | Albright . |
| 2,078,786 | 4/1937 | Wood . |
| 2,190,383 | 2/1940 | Newman . |
| 2,190,384 | 2/1940 | Newman . |
| 2,192,768 | 3/1940 | Cross . |
| 2,466,042 | 4/1949 | Reich et al. . |
| 2,734,508 | 2/1956 | Kozinski . |

(List continued on next page.)

FOREIGN PATENT DOCUMENTS

| | | |
|---|---|---|
| 0253677 | 1/1988 | European Pat. Off. . |
| 0333381 | 9/1989 | European Pat. Off. . |
| 0370890 | 5/1990 | European Pat. Off. . |
| 3516830 | 7/1989 | Germany . |
| 728858 | 4/1977 | Russian Federation . |
| 287772 | 3/1928 | United Kingdom . |
| 315971 | 7/1929 | United Kingdom . |
| 317604 | 8/1929 | United Kingdom . |
| WO90/02525 | 3/1990 | WIPO . |
| WO94/21203 | 9/1994 | WIPO . |

OTHER PUBLICATIONS

Potential Treatment of Cancer by Electromagnetic Heating; R. K. Gilchrist, M. D. Encl. 1, pp. 499–500, Apr. 1996.
Hyperthermic Therapy for Human Neoplasms; F. Kristian Storm, M. D. et al; vol. 46, pp. 1849–1854; 1980.
Effect of Marked Hyperthermia Upon the Canine Bladder; Charles Linke et a.; vol. 107. 1972.
Laser photovaporization of endometrium for the treatment of menorrhagia; Milton H. Goldrath, M. D.; pp. 14–19; vol. 140; 1981.

Primary Examiner—Angela D. Sykes
Assistant Examiner—Stephen Huang
Attorney, Agent, or Firm—Burns, Doane, Swecker & Mathis, L.L.P.

[57] ABSTRACT

A device for hyperthermia treatment in a body cavity or duct which has a narrow access pathway includes an elongate distal section for insertion into the body cavity comprising a centrally-located heat-releasing element enclosed by an elastic enclosure. The heat-releasing element is either surrounded by an elongate housing or is shaped to form a housing. An axially opening inlet passage opens to the proximal part of the housing to supply a heat-transmitting fluid to the housing. The housing has an outlet port to allow fluid to flow from the housing to fill and expand the elastic enclosure to exert pressure on the walls of the body cavity and an inlet port which allows fluid to return into the housing, thus permitting circulation of the fluid during treatment which results in uniform heating of the fluid. The heat-releasing element is formed of an inherently heat self-regulating type material and is either a semi-conductor material of PTC-type having a Curie temperature or Trip point, or a ferromagnetic material having a Curie point in combination with a supply of energy based on magnetic induction.

33 Claims, 5 Drawing Sheets

U.S. PATENT DOCUMENTS

| | | | |
|---|---|---|---|
| 2,777,442 | 1/1957 | Zelano . | |
| 2,777,445 | 1/1957 | Hart . | |
| 3,294,628 | 12/1966 | Droegemueller et al. . | |
| 3,369,549 | 2/1968 | Armao . | |
| 3,417,746 | 12/1968 | Moore et al. . | |
| 4,137,922 | 2/1979 | Leininger et al. . | |
| 4,160,455 | 7/1979 | Law . | |
| 4,546,759 | 10/1985 | Solar . | |
| 4,574,752 | 3/1986 | Reichert, Jr. et al. . | |
| 4,638,806 | 1/1987 | Bartlett . | |
| 4,676,258 | 6/1987 | Inokuchi et al. . | |
| 4,686,965 | 8/1987 | Bonnet et al. . | |
| 4,709,698 | 12/1987 | Johnston et al. | 604/114 X |
| 4,754,752 | 7/1988 | Ginsburg et al. . | |
| 4,773,899 | 9/1988 | Spears . | |
| 4,793,351 | 12/1988 | Landman et al. . | |
| 4,799,479 | 1/1989 | Spears . | |
| 4,834,091 | 5/1989 | Ott . | |
| 4,860,744 | 8/1989 | Johnson et al. | 606/31 |
| 4,949,718 | 8/1990 | Neuwirth et al. . | |
| 5,047,025 | 9/1991 | Taylor et al. | 606/28 X |
| 5,105,808 | 4/1992 | Neuwirth et al. . | |
| 5,133,710 | 7/1992 | Carter et al. . | |
| 5,151,100 | 9/1992 | Abele et al. | 606/28 |
| 5,159,925 | 11/1992 | Neuwirth et al. . | |
| 5,257,977 | 11/1993 | Eshel . | |
| 5,492,529 | 2/1996 | Neuwirth et al. . | |
| 5,499,380 | 9/1995 | Chin . | |
| 5,501,681 | 3/1996 | Neuwirth et al. . | |

DEVICE FOR HYPERTHERMIA TREATMENT

This application is a continuation of application Ser. No. 08/204,358, filed Mar. 29, 1994, now abandoned.

FIELD OF THE INVENTION

The present invention relates to an apparatus or a device for carrying out so called hyperthermia in a body cavity or body canal by heat generation. The invention also includes a method for carrying out such treatment.

BACKGROUND AND SUMMARY

Heat generated through different energy forms is used inter alia in the field of hyperthermia, which involves the treatment of tissues of different kinds with the supply of heat. Hyperthermia is particularly used for the treatment of malign tumors, whereby one makes use of the fact that certain cancer cells are destroyed at a certain temperature, for example about 42° C., whereas surrounding healthy cells remain unaffected at this temperature. Hyperthermia is also used in the treatment of certain benign conditions of disorder, for example prostate hyperplasia (BPH), where heating of the swollen prostate rectally or urethrally to a temperature range of about 44°–48° C. gives a certain positive effect, probably depending on the fact that the swelling is reduced.

Heat is utilized also medicinally in that laser beams or instruments heated by radio frequency are introduced at certain surgical operations, the tissue being burned at the same time as the blood of surrounding vessels is brought to coagulate in this manner also certain organ parts showing large flow of blood (perfusion) are treated.

A pronounced problem in hyperthermia resides in measuring and controlling the temperature in the tissue to be treated so as not to destroy surrounding healthy tissue. This is particularly the case with deeply located tissues or organs. Irrespective of the manner at which heat is treated, such as by heat conduction or through ultrasound, radiofrequent energy, microwaves, differences in the structure and flow of blood of the tissue contributes to difficulties with regard to maintaining a certain temperature or obtaining a certain depth of treatment.

The choice of method of treatment is affected by these factors and it is thus for example not possible to establish a desired temperature level by means of heat conduction from a heat source in view of the fact that the temperature drop inwardly through the tissue becomes too large depending on the cooling effect of the blood. The temperature distribution in different parts of the treated organ also often becomes uneven in view of variations in the flow of blood. Also in the treatment of more deeply penetrating methods, for example using radio frequency techniques in the frequency range up to 300 MHz or microwave techniques in the frequency range 300–2450 MHz, varying blood perfusion raises problems, partly in view of the fact that the temperature gradient inwardly in the tissue varies, partly through the fact that the temperature will vary within different parts of tissue.

As indicated above also temperature measurement constitutes a problem. It is often impossible to measure the temperature at a sufficient number of locations in the tissue volume to be treated, a condition which is aggravated by varying perfusion which results in a need of an even larger number of measuring locations.

It has been suggested in the treatment of certain tumors to introduce by operation metal needles at a certain distance from each other, said needles being made of a ferromagnetic material are capable of heating wirelessly through magnetic induction. This technique means that the needles are left for a number of treatments and in each treatment the patient is placed so that an exterior induction coil surrounds the part of the body containing the tumor involved. This coil generates a magnetic field, the intensity and strength of which affects the heat released from the needle by heat conduction. By selecting a metallic material among certain alloys having such magnetic properties as to have a so called Curie point corresponding to the desired temperature no particular thermoelements for measuring the temperature are required. Such needles of so called ferromagnetic alloys operate as if had they a built-in thermostate and also generate during the heating phase less heat the closer one comes to the desired temperature (the Curie point). The absence of equipment for temperature measurement and temperature control is, of course, a great advantage, but the drawback of this particular technique is the fact that the needles have to be capable of producing sufficient quantities of energy so as to reach the desired treatment temperature. On the other hand the needles must not be too thick or must not flex too easily, and therefore the technique is not suitable for application on organ parts where the blood perfusion is high or uneven. Another drawback associated with the technique is that it cannot be applied to the treatment of difficultly accessible tumors or intra-cavitarily.

Heat treatment has also been applied to excessive uterus hemorrhage (menorrhagia), which disorder shows very strong bleeding as a symptom. The most common measure adhered to at this disorder is uterus extraction, which is a traumatically very large surgical operation associated with certain risks and which also can result in conditions of psychical stress. Only in the United States about 0.5 million of hysterectomies are made, the majority thereof because of menorrhagia.

For a long time one has tried to develop methods for the suitable treatment of the disorder, inter alia by destroying the uterus mucosa (endometrium) by heating, for example using a laser, but this is time consuming and requires pronounced caution and skill. Attempts using microwave heating have not been very successful, since the uterus cavity is flattened and triangular shaped and the distribution of the microwaves is such as to result in a very uneven treatment. The large flow of blood in the endometrium surrounding the myometrium also results in large temperature drops in view of the cooling effect of the blood, resulting in uneven heating. There are also difficulties to protect the cervix and the vagina from burns. Moreover, experience shows that perforation of the uterus wall can take place with the treatment using a laser.

Examples illustrating prior art concerning the treatment of internal disorders while supplying heat and optionally supplying pressure are found in U.S. Pat. Nos. 4,160,455, 4,773,899, 4,799,479, 4,709,698 and 4,949,718, and the EP-application, publication No. 0 370 890 A1.

The present invention has for its purpose to provide new techniques for carrying out hyperthermia, whereby the drawbacks of the prior art are eliminated or at least substantially reduced.

One particular object of the present invention is thus to provide a device for carrying out such so called hyperthermia in a body cavity or duct in a manner which is satisfactory from a safety point of view. For these and other objects the device according to the invention includes a distal section intended to be inserted into said cavity or duct comprising a centrally located, heat-releasing element, which is either surrounded by an elongate housing or is itself constituted by an elongate housing, and a flexible and/or elastic enclosure surrounding said housing in a liquid-tight manner, further including means for supplying energy to the heat-releasing element and an axially operating inlet passage at the proximal part of the housing, an outlet from the housing being arranged for the supply of heat-transmitting medium under pressure for expansion of the flexible enclosure to accomodate to said cavity or duct and to exert a con%rolled pressure on surrounding walls. The device according to the invention further comprises a second inlet to the housing and means for internal circulation of said medium through the housing, the heat-releasing element being of an inherently self-regulating type.

As will be explained later in this disclosure heat-releasing elements of the inherently self-regulating or self-controlling type are exemplified by materials of the PTC-type, or by ferromagnetic materials where the means for the supply of energy are based on magnetic induction.

The PTC-material is a semiconductor and has a constant resistance up to a specific temperature, the so called Curie Point (CP) or trip point (TP), which is predetermined. At the trip point, the resistance increases by 100% but over this temperature the resistance increases drastically, for example 20–30% per. ° C.

When the material is connected to an electric source of a certain voltage it will emit energy in form of heat from its surfaces in such a way that the larger the surface the greater the emission will be. Because of the temperature-depending resistance, it is self-regulating with regard to heat emission at temperatures in the range of the TP, e.g. the material is capable of maintaining steady state conditions even if variations in power requirement occur at a certain temperature level.

An element containing a ferromagnetic material having a CP is also self-regulating and the material will, at a certain predetermined temperature close to the CP, cease to be ferromagnetic, and thus placed in a magnetic-field the energy emission will be drastically reduced.

According to the invention, the centrally located heating element consists of a self-regulating material of a compact design enabling access to the treatment site but at the same time providing sufficient heat-emitting surfaces to be capable to emit sufficient energy at a certain temperature level even at variations in power.

The problem of creating sufficient power output while avoiding self-inhibition associated with a compact design of the heating element has been solved in accordance with the invention by arranging the compact heat releasing self-regulating material in a surrounding elongate housing or by designing the material itself as an elongate housing with an inlet and an outlet, the heat-transmitting medium being forced through and around the material by an efficient internal circulation. Inspire of restriction in size the material can provide for sufficient power output at temperatures in the range of TP or CP, thus resulting in successful treatment under self-regulating conditions. This also means that the heat-emitting element above the predetermined temperature range of CP operates in such a manner that the energy-generation automatically will be significantly reduced and self-inhibition will occur so that overheating thereby cannot take place under any circumstances.

For the treatment of disorders of the uterus the material of the heat-releasing element may have a trip point or Curie point lying within the range about 60° C. to about 90° C., particularly about 70° C. to about 80° C. On the other hand, for the treatment of prostatic disorders said ranges may be from about 45° C. to about 65° C., particularly about 48° C. to about 56° C.

In accordance with a preferred embodiment of the invention the device contains in said elongate housing two or several, axial and parallelly arranged part-elements of PTC-type having substantially parallel surfaces. Said part-elements are suitably placed spaced from each other and from the surrounding housing wall to form canals or passages between and about the part-elements to form sufficient surface and to provide for effective and even heat-emission to the surrounding flowing heat-transmitting medium.

In order to obtain a sufficient power output the PTC-material is preferably arranged with a packing degree within said housing within the range about 35 to about 70% by volume, i.e. corresponding to a void volume of about 65 to about 30%, preferably about 45 to 65% by volume, i.e. corresponding to a void volume of about 55 to about 35%.

In such preferred embodiment the thickness of the part-elements is suitably at most about 1.5 mm and they may have a power capacity at steady state of at least about 1–1.5 W/cm$^2$ of exposed element surface at a voltage of about 24 V. In this disclosure the expression "exposed element surface" refers to the total surface of the heating element exposed to the heat-transmitting medium. Due to the lower electrical resistance at temperatures below the self-regulating temperature range the emitted power will be much higher, such as 3 times higher than at steady state, which is of a great advantage since it significantly reduces the start-up time.

For use in narrow passages in a living body said housing preferably has an outer diameter of at most about 7–8 mm, and at such dimension its capacity of heat-generation at steady state shall correspond to a release of heat of about 3 W/cm axial length or extension of the housing at the treating temperature used and at a voltage of about 24 V.

It is preferred that said means for internal circulation has a capacity at steady state conditions of replacing the void volume of the housing of said medium at least about 30 times per minute, and preferably at least about 60 times per minute.

According to an alternative embodiment of the invention said elongate housing may be constituted by a cylindrical element of PTC-type which is flown through and around by the heat-transmitting medium.

According to a particularly preferred embodiment of the invention the device may contain an inlet for the medium located in the housing on the opposite side of element relative to said outlet, and means for imparting flow to the medium in an internal circuit from the space between housing and the surrounding flexible enclosure, through housing via said inlet and outlet, for absorbing heat and through the space between housing and enclosure for the release of heat through the enclosure wall.

In such embodiment of the invention the device may be characterized by at least one first back valve arranged in association with the inlet, said back valve allowing flow into the interior of the housing, and the flow resistance of which in an open position is lower than the flow resistance through the housing, said means for the flow of the medium in an internal circuit being arranged to provide a reciprocating movement of a small quantity of the pressurized quantity of medium enclosed in the inlet canal of the device after expansion of the enclosure, whereby the inlet is closed and the outlet is open, whereby the circulation of the medium in a circuit is provided.

According to yet another embodiment of the invention the device is characterized by at least one first back valve arranged in association with the outlet allowing flow out of the interior of the housing, the flow resistance of the inlet being higher than the flow resistance through the housing, said means for the flow of the medium in an internal circuit being arranged to provide a reciprocating movement of a small quantity of the pressurized medium enclosed in the inlet canal of the device after expansion of the enclosure, whereby the inlet is open and the outlet is closed, thereby providing circulation of the medium in a closed circuit.

According to an alternative embodiment of the invention the device is characterized by an inlet for the medium arranged in the housing on the other side of the element relative to said outlet and by a partition placed between said inlet and the element or between said element and the outlet, respectively, forming a chamber and which is provided with an axial passage containing a second back valve, which is oppositely placed relative to the first back valve placed in the inlet, the means for the flow of the medium in an internal circuit being arranged to provide a reciprocating movement of a small quantity of the pressurized medium enclosed in the inlet canal of the device after expansion of the enclosure, whereby the inlet is closed and the outlet is open or the inlet is open and the outlet is closed, respectively, thereby providing circulation of the medium in a closed circuit.

It is preferred in the device according to the invention to provide two oppositely placed back valves in connection with the inlet and the outlet. Said partition is suitably placed between the inlet and the element.

The back valves used in association with the present invention can be of any conventional type. As examples there may be mentioned flap valves, ball valves, disc valves, etc. Flap valves are preferred in view of their simple design.

Said means for providing flow of the medium may, in accordance with a preferred embodiment of the invention, be arranged to provide for a volumetric flow of the medium. Such means may comprise a reciprocating piston.

According to an alternative embodiment of the device according to the invention said means for the flow of the medium in an internal circuit include a propeller or an axial pump wheel placed between the radial inlet and outlet.

As an alternative, to provide for circulation of the medium the device according to the invention may contain means comprising a reciprocating piston provided with one or several axially directed apertures and corresponding back valves.

In another embodiment of the device according to the invention said distal section comprises a central tubular element and a number of parallel, longitudinally extending bars, bands or wires of a ferromagnetic material essentially evenly distributed around said tubular element and constituting said means for heat generation. The metal alloy used suitably essentially consists of nickel and copper, nickel and silica, iron and platinum or iron and palladium.

In such an embodiment the device includes means for the supply of energy comprising an induction coil intended to surround the body or body part containing said body cavity or duct. It is preferred that the ferromagnetic material has a substantial extension in the direction of a magnetic induction field. To obtain the necessary power output from the compact element the ferromagnetic material is suitably designed with a packing degree lying within the range about 25 to about 60%, i.e. corresponding to a void percentage of about 40 to about 75% by volume.

Also as indicated above, the device according to the invention is particularly suited for the treatment of disorders in uterus, for example menorrhagia. Alternatively, the device according to the invention can be used for the treatment of prostatic disorders.

The invention also includes a method for carrying out so called hyperthermia in a body cavity or canal, i.e. with the supply of heat to said body cavity. Such hyperthermia is carried out with simultaneous application of a controlled pressure against the tissue surrounding the body cavity. This method is characterized by the fact that the supply of heat is provided by using a heat-releasing system of a self-controlling or self-regulating type. As previously mentioned the method is particularly suited for the treatment of disorders in the uterus or in the prostate.

In connection with the use of a self-regulating system containing a semiconductor material of PTC-type is particularly preferred from a safety point of view to feed the semiconductor material using a low-voltage current, for example having a voltage of at most about 50 V and particularly at most about 30 V. Using available semiconductor materials of PTC-type even lower voltages can be used, such as down to 20 to 25 V, enabling use of rechargeable batteries. This excludes the risk for electric shocks.

BRIEF DESCRIPTION OF THE DRAWINGS

The controlled pressure used in combination with heat supply is suitably at least a pressure lying within the range between diastolic pressure and systolic pressure.

The invention will in the following be further described by exemplifying embodiments which, however, must not be considered to restrict the scope of protection as defined in the appended claims. These embodiments are described in connection with the appended drawings, wherein:

DETAILED DESCRIPTION

According to the invention a self-regulating system is used, i.e. a system wherein the energy generation falls rapidly at a certain predetermined temperature in dependence on properties of the heat-emitting material. Two practical examples are presented below.

In a preferred embodiment according to the present invention the heat-emitting element is constituted by a semiconductor material of a certain character, a thermistor of PTC-type (Positive Temperature Coefficient). This material consisting of a ceramic material usually originating from $BaTiO_3$ has the property that the electric resistance is dependent on the temperature in such a manner that the resistance is constant and low up to a certain temperature, the so called Curie temperature or trip point, whereas the resistance increases rapidly if the temperature exceeds the Curie or trip point temperature. Such semiconductor materials are presently sold by for example Siemens and Philips and are used practically for heating, for example in ironing devices for travelling, rear view mirrors etc. As mentioned earlier the self-regulating material according to the best mode of the invention is enclosed in an elongate housing or constitutes itself the elongate housing which diameter shall not exceed 7–8 mm and preferable not 5 to allow the housing which constitutes the distal end of the catheter to pass through narrow passages such as the cervix canal or the urethra. There is also a limitation in length of the energy emitting part of the housing. When used for the treatment or uterus it is preferred that the length is not longer than the depth of the uterus which normally is between 30 to 80 mm. The reason is that it is not desirable that the cervix canal is heated. In case of the treatment of prostatic disorders there is also a limitation in length determined by the distance between the sphincter and the bladder.

Consequently the volume of the heat emitting part of a housing with a length of 3 cm shall not have a volume of more than about 1.5 $cm^3$, preferably not more than 0.6 $cm^3$ equal to 0.2–0.5 $cm^3$/cm length. The corresponding heat emitting surfaces are about 4.5 to 7.5 $cm^2$—these numbers only given as examples.

Trials have shown that high energy emissions are necessary under treatment to compensate for the heat losses through the uterus wall, which has a surface of about 14–40 $cm^2$, e.g. 3 to 10 times larger than that of the heating element.

Trials have also shown that there is a need of power of about 8–40 W to compensate the heat losses in the treatment of uterus, i.e. at the temperature where self-regulation occurs, depending on the specific circumstances, such as the penetration deep of heat, blood perfusion, size of the uterus cavity. Even if a large and deep uterus allows a longer heat emitting part there is a minimal need of about 3 W per cm length for a device according to the invention. For the treatment of a deeper and larger uterus a longer emitting part however can compensate for the larger need of power.

The PTC material can be produced in many different shapes. For the use as heating elements for some of the embodiments according to the invention it is preferred to use elements in flat or tubular forms. A flat PTC material has normally a thickness of about 1 mm or more. The two sides are covered with a layer of electrical conductive material. When the two sides are connected to an electric source heat is developed in the material depending on the resistance of the material. The amount of heat at a certain temperature below the TP is depending of different factors, such as the material characteristics, the voltage applied but also the size of the surface. One advantage is that considerable amounts of heat can be emitted from a certain surface area.

To be able to fulfill the requirement to have a minimum emission capacity of 3 W per length cm in a housing of 0.2–0.5 $cm^3$ per cm length as mentioned as examples above the material however has to be enclosed and packed in the housing in a very dense way.

Experiments have shown that to achieve sufficient power emission capacity the packing degree of PTC material will be between about 35–70% of the total volume of the housing. As mentioned earlier such high density causes self-inhibition even if there are arranged passages in between elements of the PTC material, unless an efficient circulation of a heat-absorbing medium is provided.

According to the invention these passages are filled with a heat-absorbing medium in form of a liquid which is forced to pass through the passages in the housing. By an effective circulation of the liquid the emitted heat is taken up by the liquid at its passage through the passages in the housing and brought out through the outlet into the outer space between the housing and the expanded enclosure to compensate for the heat losses through the enclosure to the surrounding endometrium. It is preferred that the circulation means consist of a volumetric pump to provide for an efficient circulation of liquid in spite of the resistance imparted by the narrow passages. Under the condition that the flow of circulating liquid, e.g. water, is sufficient, the amount of emitted energy in the form of heat from the element will at steady state conditions compensate for the heat transfer to the endometrium.

Figure 6:
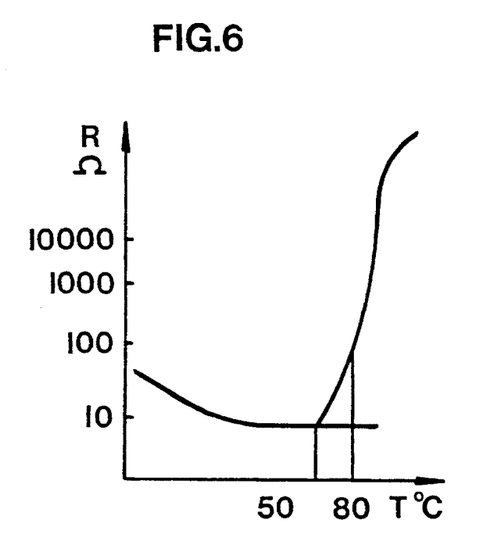
FIG. 6 shows a diagram on electric resistance as a function of temperature for a PTC-material used.

The temperature-resistance curve for a suitable PTC-material is shown in FIG. 6. A PTC-material having a suitable Curie point and a relation between resistance and temperature in principal similar to that of FIG. 6 becomes self-regulating as regards the generated power at the temperature desired for the treatment. Thus, for example a suitable material having a Curie or trip point of about 70° C. (see FIG. 6) and is supplied with 20 volts can generate up to about 20 W/cm length of element during the heating-up phase and about 7 W/cm length at a temperature of about 65°–70° C. However, if the temperature exceeds 80° C. the generated energy falls drastically, and self-inhibition occurs after a few degrees increase. In hyperthermia according to the invention it is possible to maintain uterus surface at a desired treatment temperature, for example about 70° C. One condition for this is that the corresponding energy requirement to cover the heat losses out into the uterus wall can be provided. In view of the properties of the PTC-material and as is clear from FIG. 6 the heat release will automatically adjust so as to correspond to the power needed at a specific moment. If the cooling from the uterus wall for some reason suddenly increases the surface temperature drops somewhat resulting in an increased heat release from the PTC-material. On the other hand the temperature cannot exceed a certain value if for example the power requirement becomes very small. In other words, the material never becomes hotter than this highest temperature, for example 80° C., which makes this system totally safe and cannot result in overheating.

There are other advantages of the said PTC-material as a heat-emitting medium. Since the system is self-regulating with regard to energy and temperature no more or less complicated thermometry will be needed, nor a more or less sophisticated control system. Furthermore, the device is suitable for mass production and to a low cost therefore making it suitable as a disposable.

In another preferred embodiment of the invention the heat-emitting medium is a ferromagnetic material having a Curie point adapted to the purpose, for example in the form of elongate wires.

The energy necessary for the heat treatment is supplied wire-lessly through magnetic induction to the ferromagnetic material which generates heat, on the one hand through eddy currents, on the other hand through hysteresis losses. There is a large number of such materials known. It has been found that a suitable frequency range is 50–120 KHz and a suitable field strength is of the order 4000 A/m and the direction of the magnet field should coincide with the orientation of the wires for optimum energy generation.

In view of the fact that the ferromagnetic material consists of an alloy having a Curie point differing some degrees from the desired temperature no control or regulating system will be needed.

As examples of suitable alloys there may be mentioned copper-nickel, silicon-nickel, iron-platinum and iron-palladium alloys. For copper-nickel suitable proportions are about 30% by weight Cu and 70% by weight Ni. By careful choice of the proportions Cu-Ni and a suitable mechanical and thermal treatment of the alloy the material can be given a Curie point with an accuracy of some degrees.

In this case, as well as when using the PTC-material described earlier, it is important that a heat-absorbing and heat-releasing medium effectively takes care of the heat transport out of the heat-emitting material to the interior surface of the cavity that shall be treated, in this example the endometrium. As in the case with the PTC-material the ferromagnetic wires are self-regulating so that the released heat can be adapted to the heat requirement at a certain temperature. Also in this case it is a requirement that the diameter of the central body is small and preferably does not exceed about 5–7 mm. This means that the ferromagnetic wires must be placed closely adjacent to each other in order that a sufficiently high energy generation shall be obtained. Also in this case the circulation device having a volumetric pump device as described earlier will meet the requirement of good circulation in spite of the large resistance imparted by the closely located ferromagnetic wires.

Figure 1:
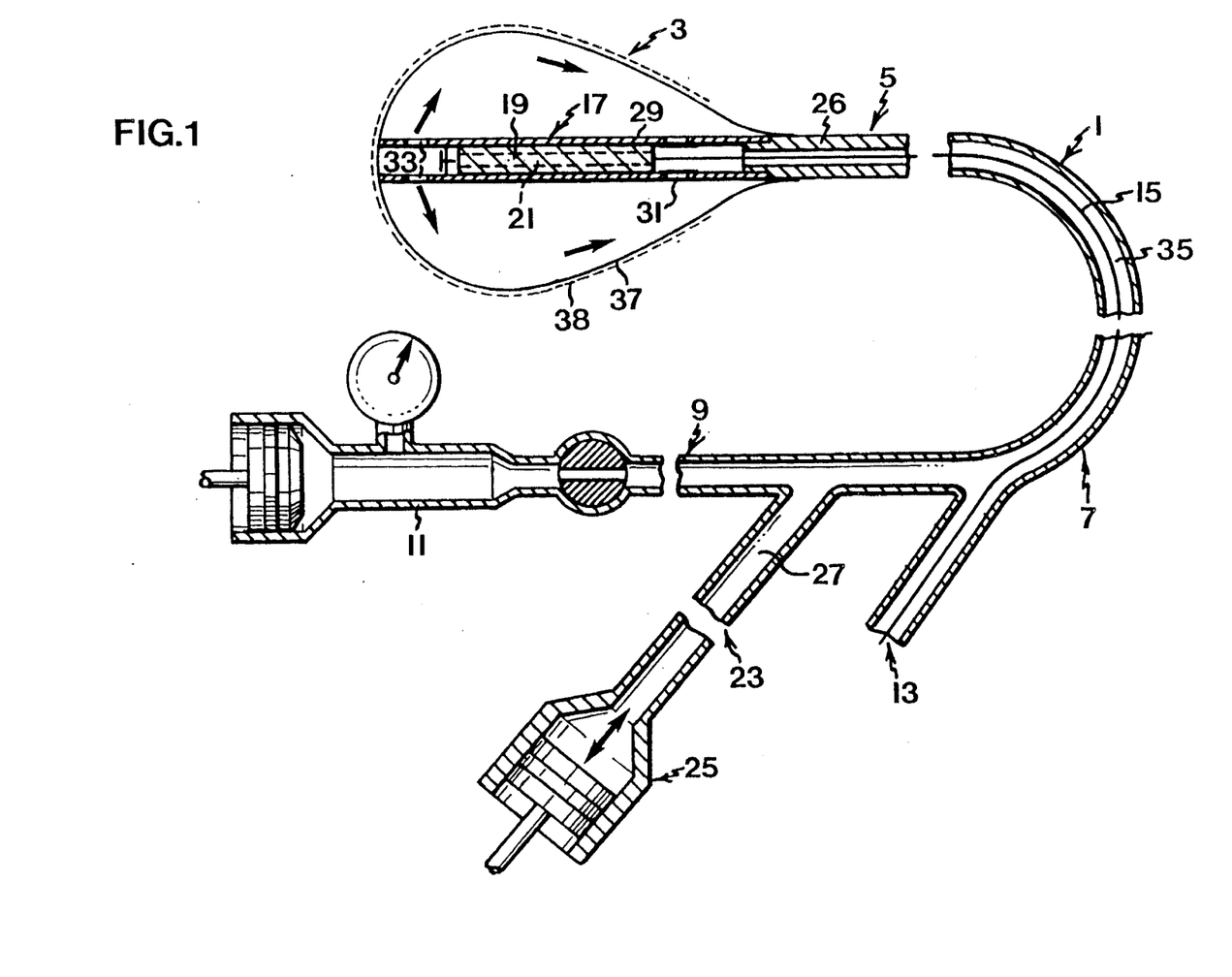
FIG. 1 illustrates diagramatically an embodiment of the device according to the present invention working with pulsating pressure.

The device according to FIG. 1 includes a heat applicator 1 in the form of a catheter of a disposable type, the distal part 3 of which is intended to be inserted into the body cavity, for example the uterus cavity, that shall be heat treated. The applicator has an intermediate part 5 for facilitating insertion of the distal part 3 and for fixation of the position of part 3 in the cavity. The proximal part 7 of the applicator has connecting means 9 for the supply of a compressed medium, for example a liquid from an apparatus 11, for the generation and measurement of pressure via an inlet canal 35 associated with the applicator. Furthermore, the applicator has a connecting means 13 to an electric energy source, not shown, so that an electric current via a cable device 15 can be supplied to a central body 17 containing inter alia a heat-emitting element 19 of a self-regulating type, such as PTC-type, and canals or passages 21 arranged therein or thereabout. Furthermore, the applicator has connecting means 23 to an apparatus 25 for the generation of oscillating pressure impacts to the inlet canal 35 of the applicator after it has been filled with pressurized liquid from apparatus 11. The central body 17 is surrounded by a thin flexible and elastic enclosure or balloon 37 which is brought to expand when the pressure medium is supplied to the interior of the enclosure through canal 35.

The central body 17 with the heat-emitting element 19 has an elongate shape and has a housing 29 surrounding element 19, the housing being provided with apertures 31 in its proximal part and apertures 33 in its distal part.

Figure 2:
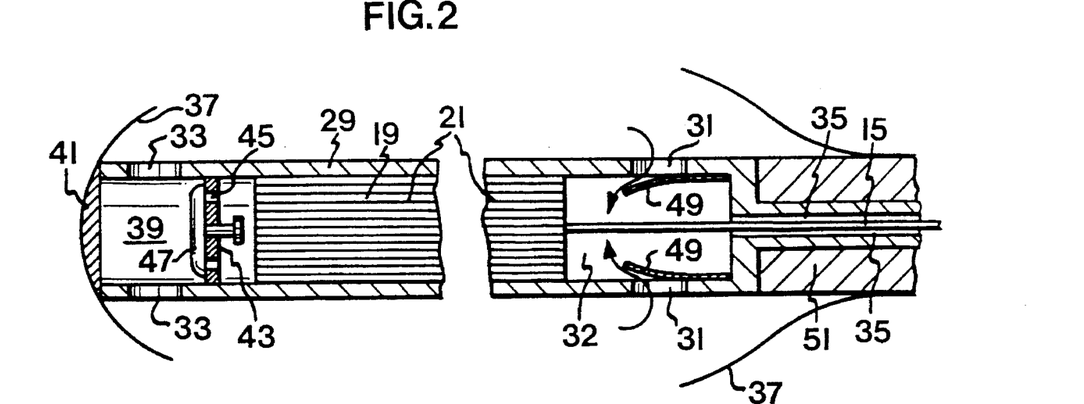
FIG. 2 shows in enlargement a section through the interior central distal part of the device shown in FIG. 1.

FIG. 2 shows in detail of the embodiment according to FIG. 1 a system for enabling effective heat transport and heat transfer from the heat-emitting element 19 to the uterus mucosa (endometrium). Apertures 31 in the proximal part of the tubular central body act as radially acting inlets for a pressurized liquid to a valve housing 32 communicating with the inlet canal 35, the space between central body 17 and enclosure 29, as well as with canals 21 arranged about and through the heat-emitting element 19 in the middle part of the central body. Apertures 33 arranged in the distal part of the central body act as outlets for the pressurized liquid from a second valve housing 39 communicating with canals 21 and the space between the central body 17 and the elastic enclosure 37, said enclosure being liquid-tight sealed around the proximal part of the central body at 51 and being attached to the nose member 41 of the central body. In valve housing 32 back valves 49 are arranged so as to close apertures or openings 31 at overpressure in the valve housing 32 and opening at a sub-pressure relative to the liquid pressure in the space between central body 17 and the elastic enclosure 37. A partition 43 having openings 45 is arranged in valve housing 39. A disc valve 47 is moveable in axial direction and arranged so as to close openings 45 at overpressure in valve housing 39 relative to the liquid pressure in canals 21 in the heat-emitting element of the central body or opening at sub-pressure in valve housing 45, respectively.

During heat treatment of for example uterus using the device according to FIG. 1 means 9, 13, 23 are connected to the respective apparatuses for the supply of pressurized liquid, electric power and for the generation of oscillating pressure impact. Then the distal part 3 of the applicator is inserted through cervix into the uterus cavity up to the bottom of the cavity. The length of central body 17 corresponds approximately to the length of the uterus cavity, i.e. normally 4–5 cm. Pressurized liquid is then supplied to the applicator through apparatus 11 via the inlet canal 35, back valve 49 closing apertures 31 and disc valve 47 being open, whereby the thin flexible and elastic enclosure 37 in the form of a balloon expands so as to conform to the uterus cavity and bring the enclosure to adapt to the contoure of the cavity and to completely engage under pressure the endometrium of the cavity, i.e. in the position shown in FIG. 1. By means of the apparatus 11 for the generation of pressure the liquid pressure is then maintained at a level suitable for the treatment, which shall be described later.

Then apparatus 25 having an oscillating volumetric pump, for example a piston pump, is started. At every positive pressure shock a certain volume of liquid is brought to move forward through the inlet canal 35 of the catheter body, which has for an effect that simultaneously a corresponding quantity of pressurized liquid is forced through canals 21 in the central body 17 in view of the fact that valves 49 are closed at the same time as valve 47 is opened and a corresponding quantity of pressurized liquid will be pushed out into the space inside the balloon enclosure 37. In view of the pressure increase balloon enclosure 37 and the uterus muscle surrounding same will be somewhat extended, which has been indicated with dashed lines 38 in FIG. 1.

At every subsequent withdrawal in the movement of the piston pump a corresponding liquid quantity will be sucked back, valves 49 taking the open position shown in FIG. 2 and valve 47 its closed position. The enclosure takes at the same time its original position according to the full line 37 in FIG. 1.

It is appreciated that under the influence of the oscillating pressure shocks and the described valve system a powerful and effective circulation in an internal flow circuit of liquid at the pressure given by pressure apparatus 11 will be provided through canals 21 of the central body 17 and out into the space within the balloon enclosure and back to the central body without hot liquid passing the inlet canal 35 of the catheter to connecting means 23. Circulation thus takes place only in the distal part 3, whereas the inlet canal 35 during the circulation only serves as a communication conduit for transmitting in a hydraulic manner the oscillating pressure and liquid movement provided by the pump apparatus 25. Therefore, the canal can have a relatively small diameter but should be flexible and should not expand significantly in a radial direction at the pressure increase in view of the strokes of the pump. In view of the small diameter of canal 35 space is admitted for a heat insulation 26 surrounding the intermediate part 5 of the catheter in order to protect the delicate cervix during treatment. In view of the circulation system described an effective circulation of liquid is made possible also through canals 21 which in certain embodiments offer a great resistance, which shall be described later. Another advantage is the fact that the quantity of circulating liquid is determined by length of stroke and frequency of the pump and that thus the quantity can be controlled and varied in a simple manner and is independent on different changes in circulation resistance, as for example different sizes and shapes of the cavity.

A preferred liquid for use as a heat-emitting medium is water, either as such or as an isotonic salt solution. In the embodiment described and for the treatment of menorrhagia, it is preferred that the circulation through the housing is at least about 5 ml/min and per cm axial length of the element after reaching steady state conditions, i.e. the temperature of treatment.

In the circulation device described with reference to FIGS. 1 and 2 the circulation takes place by the liquid first being forced into the proximal part of the central body 17 and will then leave the distal part of the central body. It is understood that a reversed direction of circulation can be obtained if for example back valves 49 are arranged at the outside of openings 31 and the disc valve 47 is mounted reversely in the partition 43 so as to open for apertures 45 at an overpressure in valve housing 39.

The heat-emitting element 19 can have different designs within the scope of the invention. When selecting a system for heat generation the safety aspect must, however, be decisive. Thus, it is important that the risk for electro shocks in view of defect parts is excluded. There are in principal two solutions to this problem according to the invention. In the case that electric energy is supplied through cables to an element of the PTC-type the risk for electro shocks is avoided by the fact that the necessary energy can be obtained at a current supply under low voltage preferably not exceeding about 24 volts, especially when supplied from a battery. Another solution is that the heat-emitting element is supplied with energy in a wire-less manner by electro magnetic influence.

Another requirement from a safety point of view is the fact that the temperature necessary for the treatment of the tissue can be maintained during the course of treatment and that this temperature will not be exceeded. There is a further requirement that the different parts that constitute the central body must not be overheated. Otherwise there is a risk that for example housing 29, if this comes into contact with the enclosure 37 the latter may be punctured. Furthermore, the patient may be subjected to burns. These requirements for safety are fulfilled in the different embodiments within the scope of the invention.

It has been found important for the result of the treatment that the temperature necessary for the treatment can be maintained over the whole of the surface to be treated and that the necessary energy requirement for maintaining the temperature can be accomplished and that sudden changes in energy requirement in view of for example variations in blood pressure of the patient can be met quickly by a corresponding change in the power output.

These claims can be met by different embodiments within the concept of this invention. In view of the fact that the heat-emitting element 19 emits its heat to the flowing liquid said liquid will in turn release its heat over the whole of the surface of the uterus mucosa by heat conduction through the thin enclosure 37. In this manner large quantities of heat can be supplied over the whole of the uterus mucosa.

By the device shown in FIG. 1 the enclosure, as mentioned, can be brought by influence of pressure to conform to the contours of the expanded cavity and in this manner enable simultaneous treatment of the whole surface. With the device according to the invention there is also obtained another important advantage, since one by suitable choice of pressure through pressure effect on the mucosa and the underlying tissues can restrict the flow of blood in veins and arteries and in this manner reduce or completely prevent the cooling effect of the blood on the heat supplied from the central body by heat conduction. It has been surprisingly found, that the heat conductivity increases manyfold in a tissue flown through by blood and subjected to pressure as compared to the same tissue without pressure. It has also been found that the heat treatment becomes more even both laterally and depthwise.

Figure 3:
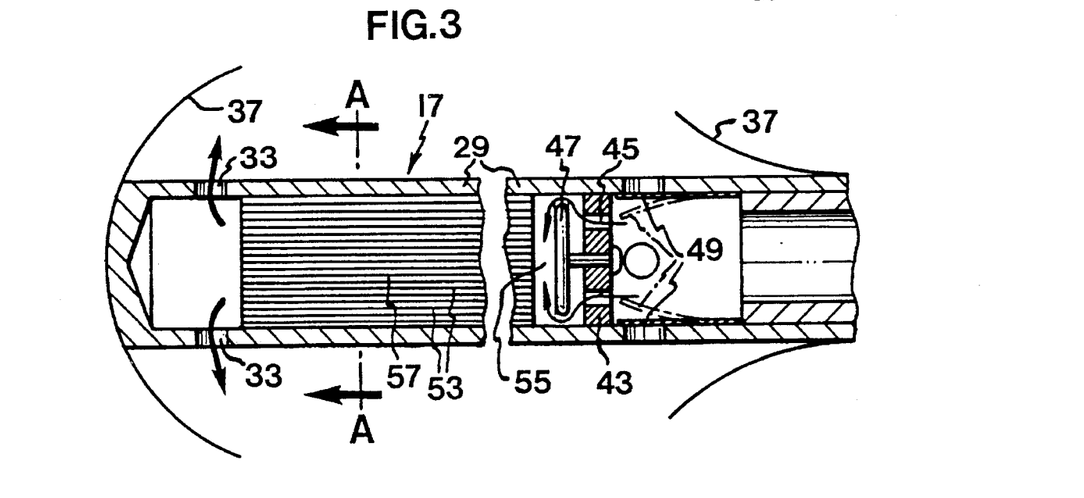
FIG. 3 shows a corresponding detail in enlargement of an alternative embodiment of the detail of FIG. 2.

FIG. 3 shows in detail a central body 17 containing parallelly extending ferromagnetic wires 53 surrounded by a housing 29, otherwise largely corresponding to the device of FIG. 2 but with the difference that the disc valve 47 and the associated partition 43 with apertures 45 are now arranged in the proximal part of central body 17. Between the inlet side of the wires and the partition 43 a chamber 55 is arranged.

FIG. 3 shows how the circulation liquid is forced into chamber 45 and further in through the wire package 57 at a pressure shock at the same time as valves 49 close apertures 31.

Figure 4:
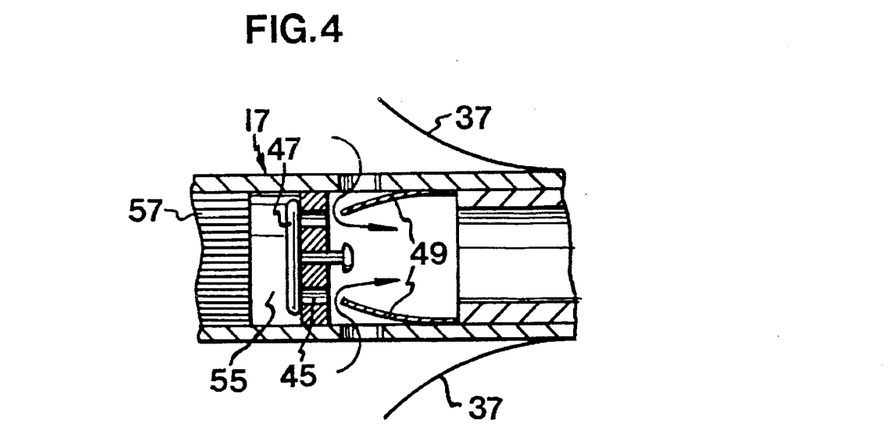
FIG. 4 shows the rear part of the detail of FIG. 3 having the valves in question in opposite positions.
Figure 5:
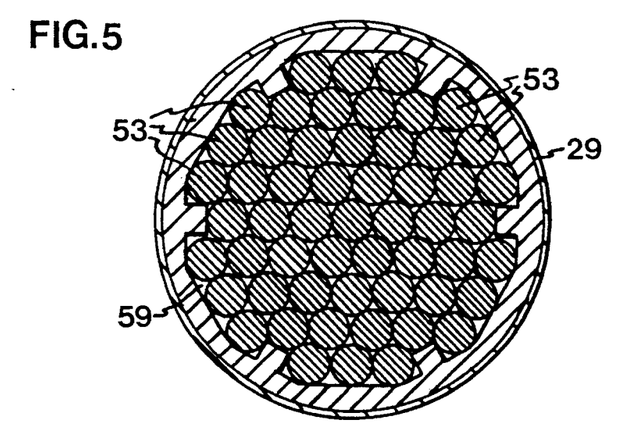
FIG. 5 shows in a cross-section and in an enlargement a section along arrow A—A in FIG. 3.

FIG. 4 shows in a detail of FIG. 3 the proximal part of central body 17 how the valve 45 is closed and the valves 49 are opened, respectively, at the reciprocal motion of the circulation pump. Also in this case the heat emitting wires offer a large resistance against circulation. This is clear from FIG. 5 showing a section A—A through the central body according to FIG. 3. The ferromagnetic wires 53 having a diameter of about 0.7 mm and a length of about 30 mm are arranged to come close into each other surrounded by housing 29 to enable as great energy generation as possible within the given diameter of housing 29 which is about 5 mm. The circulation liquid shall pass between the narrow passages extending longitudinally between wires 53 which is enabled by the circulation system described in accordance with the invention.

In FIG. 5 the heat-emitting medium is constituted by 55 wires having a diameter of about 0.7 mm. This embodiment can give a maximum power of 50 W at a frequency of the magnetic field of 90 KHz and a field strength of about 4000 A/m.

Figure 7:
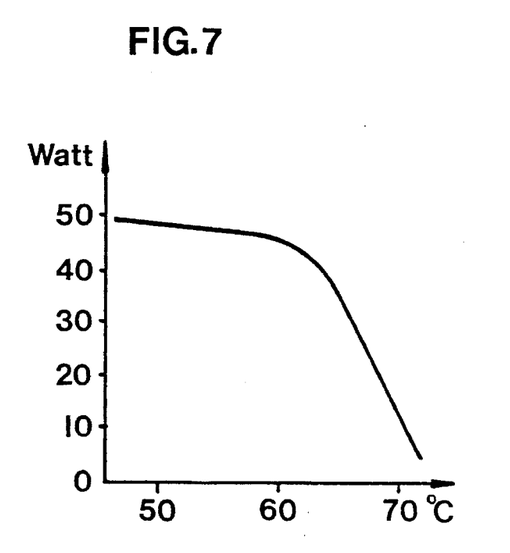
FIG. 7 shows a diagram on the power output as a function of temperature for a ferromagnetic material.

FIG. 7 shows the results of experiments giving the relation between generated power in watts of a central body according to FIG. 5 with a ferromagnetic alloy, the temperature of the surrounding liquid being measured in a calorimetric manner. The Curie point is about 75° C., the frequency 100 KHz and the output of the induction apparatus 1 KW.

As seen from FIG. 7 the energy generation in this case is about 40 W up to a temperature of about 63° C. The energy generation then strongly drops at increasing temperature to be nearly zero at the Curie point about 75° C. In hyperthermia according to this embodiment of the invention this means that the liquid is first rapidly heated until approaching the desired operating or treatment temperature. Then the energy generation falls until equilibrium between added energy and heat losses at the operating temperature. As is clear from the table a power change of 5 W results in a temperature change of about 1° C. In view of the fact that the tissue is compressed so that the blood perfusion can be reduced or wholly eliminated in accordance with the invention the system can thus maintain a very even temperature. When treating for example uterus also the advantages obtained that variations in the thickness of the mucosa and differences in blood vessel structure between different patients have a very small influence on the result when using instruments that are calibrated for a certain operating temperature, as in the above shown example about 68° C.

The advantages of the embodiment of the invention just described are obvious. Through the wire-less energy transfer there is obtained a safe system, and with the self-regulating heat-emission the applicator is substantially simplified and made cheaper. It can be mass-produced at a low cost and is suited for disposal. In view of the absence of temperature sensors with conduits and control systems the risk for for example over-heating in view of defect parts are eliminated which otherwise could have catastrophic consequences. Furthermore, metallic sensors are affected by the magnet field, whereas non-metallic sensors based on for example fibre optics are very expensive.

Figure 8:
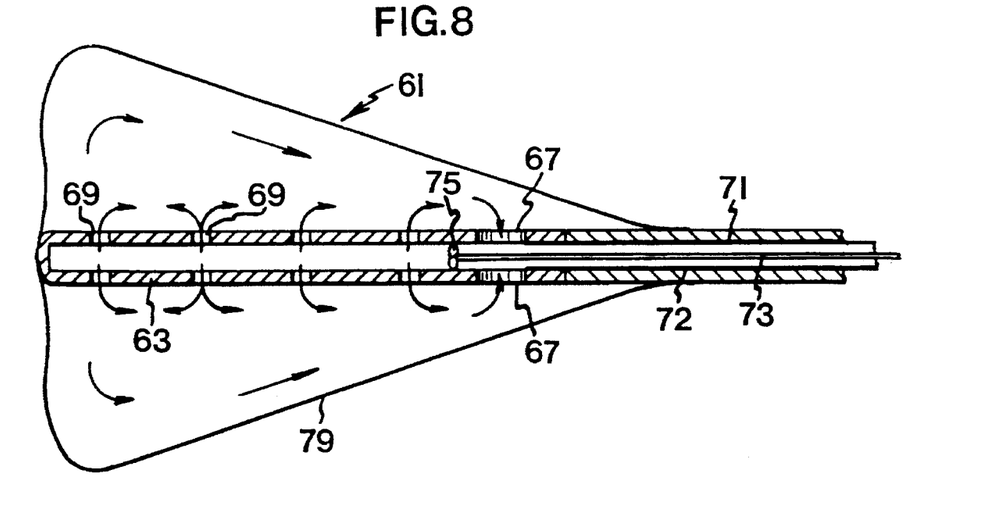
FIG. 8 shows yet another embodiment of the device according to the invention, more particularly its distal part with alternative means for providing an internal flow circuit.

FIG. 8 shows in detail the distal part 61 of a catheter. The catheter has a design similar to that of FIG. 1, i.e. it has connecting means for a pressure source for the supply of liquid under pressure and connecting means to a cable for the supply of electric energy (not shown) for the generation of heat. The connecting means described in FIG. 1 for oscillating pressure is, however, not present. The necessary circulation is, instead, performed in a mechanical manner by means of a rotating flexible shaft 73.

Central tube 63 consists of a PTC-material and has inlet apertures 67 and outlet apertures 68 for a flow of liquid distributed along and around the tube. The current leads 71,72 for the element are connected to the inside and the outside, respectively, of the PTC-tube. The shaft 73, which is connected to a driving motor not shown in the figure, imparts fast rotation to a propeller or a pump wheel 75. Through this the energy will be converted to heat, primarily within the cylindrical volume of tube 63. In view of the fast rotation of the pump wheel the liquid will be brought to circulate in a circuit from the inlet apertures 67 through the central tube 63 out through the outlet apertures 68 and via the space between the enclosure 79 and the central tube 63 back to the inlet 67, thus removing heat from the inner surface as well as the outer surface of tube 63.

Since in this case the passage through the central tube does not offer significant resistance it is sufficient with a propeller to obtain sufficient circulation of the liquid.

The choice of pressure in hyperthermia treatment according to the invention is dependent on the disorder to be treated. When treating for example menorraghia high pressures have to be used, since the uterus musculature is yielding at the same time as the mucosa or endometrium and underlying functionalis and basalis layers have a rich flow of blood. By selecting a pressure of at least the diastolic pressure, i.e. about 80 mm Hg, and in certain cases up to the systolic pressure, i.e. about 150 mm Hg, the flow of blood through endometrium can be interrupted and the desired destruction of the basalis layer can be obtained by simultaneous influence of heat, whereby the disorder can be eliminated.

Figure 9:
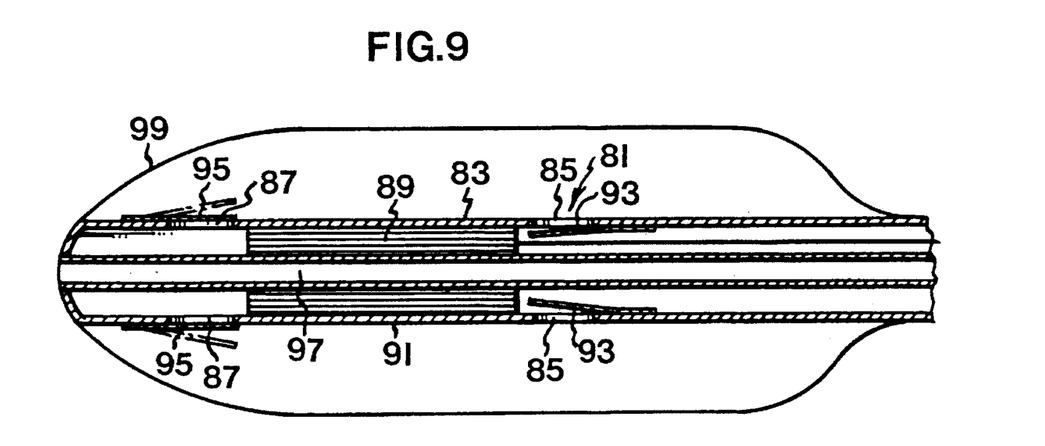
FIG. 9 shows another embodiment of the device according to the invention, i.e. the distal part thereof, suitable for the treatment of for example prostate hyperplasia.

When treating for example benign prostate hyperplasia (BPH) there is suitably used an applicator in the form of a catheter, the distal part of which is shown in FIG. 9. The applicator, the outer diameter of which should not exceed about 7 mm, is inserted into the urethra through penis so that its effective heat-emitting distal part covers the area between the sphincter and the urinary bladder. In the housing 83 of the central body 81 there are proximal inlet apertures 85 and distal outlet apertures 87 arranged. A cable for electric energy is connected to a heat-emitting element 89 with canals 91 for liquid. The heat-emitting element can be the previously described PTC-semiconductor. The circulation can suitably take place in accordance with the previously described pumping using pressure shocks. In such a case the inlet and outlet apertures are suitably provided with back valves 93 and 95, respectively, according to FIG. 9. A through-going passage 97 is arranged through the center of the applicator for the use of guide-wire or endoscope for positioning.

Alternatively, the correct positioning can be provided by an expandable balloon attached to the distal part of the applicator. In this case the positioning takes place by inserting the applicator so far that part of the distal section enters the urinary bladder. The balloon is then blown up and the applicator is retracted until the expanded balloon prevents further retraction. A suitable treatment temperature is about 45°–55° C. for a period of 60 min. The selected pressure can advantageously be high, such as within the range about 2–4 atmospheres which not only increases heat penetration but also contributes to enlarge the restriction in a mechanical way. Thus, it has been found possible to treat certain forms of BPH using a heat applicator according to FIG. 9, but where the enclosure 99 is constituted by a flexible polymer material but with limited elasticity. The enclosure, which suitably is preformed to a diameter of about 25–30 mm, is connected to a source of pressure of several atmospheres. The combination of compression of the swollen prostate and heat influence of the tissue around the urethra seems to give a useful effect, such as the formation of a necrosis which is then transformed to connective tissue. This will cause enlarging and strengthening of the urethral duct preventing renewed narrowing of the urethral passage way.

According to an alternative embodiment of the device according to the invention showing great similarities with that shown in FIG. 8 an alternative system for providing the internal circulation is used. Instead of using a propeller or pump wheel in accordance with FIG. 8 such alternative device uses a reciprocating piston which is connected to a shaft that instead of rotation performs a reciprocating movement. Such piston is provided with axially directed apertures and associated back valves, such as flap valves. At the reciprocal motion of the piston internal circulation of liquid will be provided.

Figure 10:
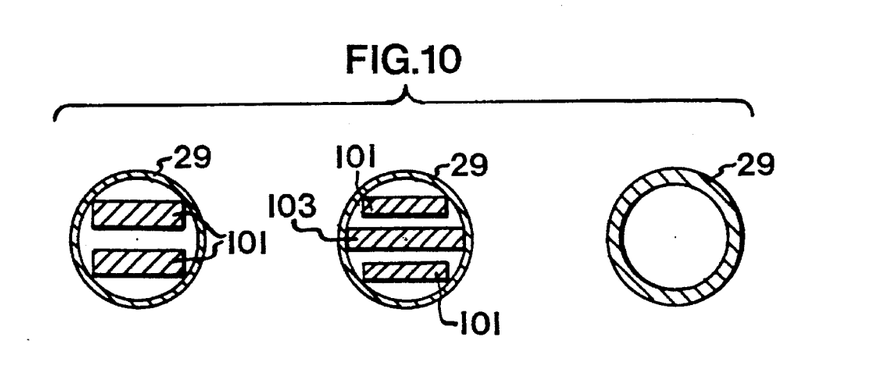
FIG. 10 shows in a cross-section different embodiments of heat-emitting elements containing a PTC-material.

FIG. 10 shows in cross-section some preferred embodiments of central elements containing PTC-material in accordance with the invention and the appended Table 1 shows the extraordinary high power outputs that can be obtained from such elements even when the outer diameter of the central tube is small. For comparison an effective length of the element amounting to 30 mm has been chosen, which is a length matching for example an instrument corresponding to that shown in FIGS. 1 to 4 for the treatment of for example uterus.

As previously indicated it is desirable for passage of cervix that the outer diameter of the central tube is less than about 7 mm for practically useful performance.

According to FIG. 10, in the PTC-elements of type 1 and of type 2, the central body is designed from a thin cylindrical housing corresponding to housing 29 in FIG. 1. In said housing several axially extending parallel thin plates 101, 103 of a PTC-material are arranged. In these examples there has been used as a PTC-material one manufactured by Siemens in the form of thin plates having a thickness of 1.1 mm and having the designation P350 and a Curie point of about 80° C. These plates have metalized planar surfaces to which current leads can be connected, for example by soldering. When a voltage of for example 24 V is supplied to the leads heat will be generated in the interior of the plate and a temperature gradient towards both surfaces of the plate will be obtained, in view of which said surfaces are in contact with circulating liquid in order that the desired power output shall be obtained.

It has now been found that by arranging the plates with axial extension in several layers using a certain space in between the layers within the housing, as shown for example by types 1 and 2 of FIG. 10, it is possible to obtain a very high power density, at the same time as longitudinally extending passages are formed between the surfaces of the plates and the walls of the surrounding housing, said passages offering a certain flow resistance, yet enabling effective flow of liquid. As an example the space in between the plates of type 2 is about 0.5 mm. It is preferred that the circulation in these two cases is provided by a volumetric pumping as previously described in connection with FIGS. 1 to 4.

In the embodiment according to type 3 of FIG. 10 the central body is constituted by a tube of PTC-material. The resistance against flow of liquid for removal of heat from the outer and inner surfaces of the tube is in this case low and can, accordingly, be provided using a propeller or pump as described in connection with FIG. 8.

In appended Table 1 recorded values on maximum and total generated power output at a voltage applied to the planar surfaces of the PTC-material of 24 V are given. By maximum generated power output is here understood the output generated at the beginning of the treatment when the circulating liquid has a temperature of about 37° C. The power output will then, in view of the self-regulating capacity of the PTC-material, decrease when approaching the desired treatment temperature as described above. However, it is generally a fact that the higher the maximum output of the central body is, the higher is the output it can generate at a certain treatment temperature provided that sufficient circulation of liquid can be maintained.

From Table 1 it can be seen that a maximum output of about 60 W will be generated by Type 1 at an outer diameter of 7 mm and a length of 30 mm, whereas for Type 2 the same effect will be obtained at a diameter of 6 mm and for Type 3 the diameter of about 5 mm. The alternative to be chosen is dependent on other factors, such as cost of manufacture, suitability for mass production etc. However, it has been found that all three alternatives give fully satisfactory treatment results.

Figure 11:
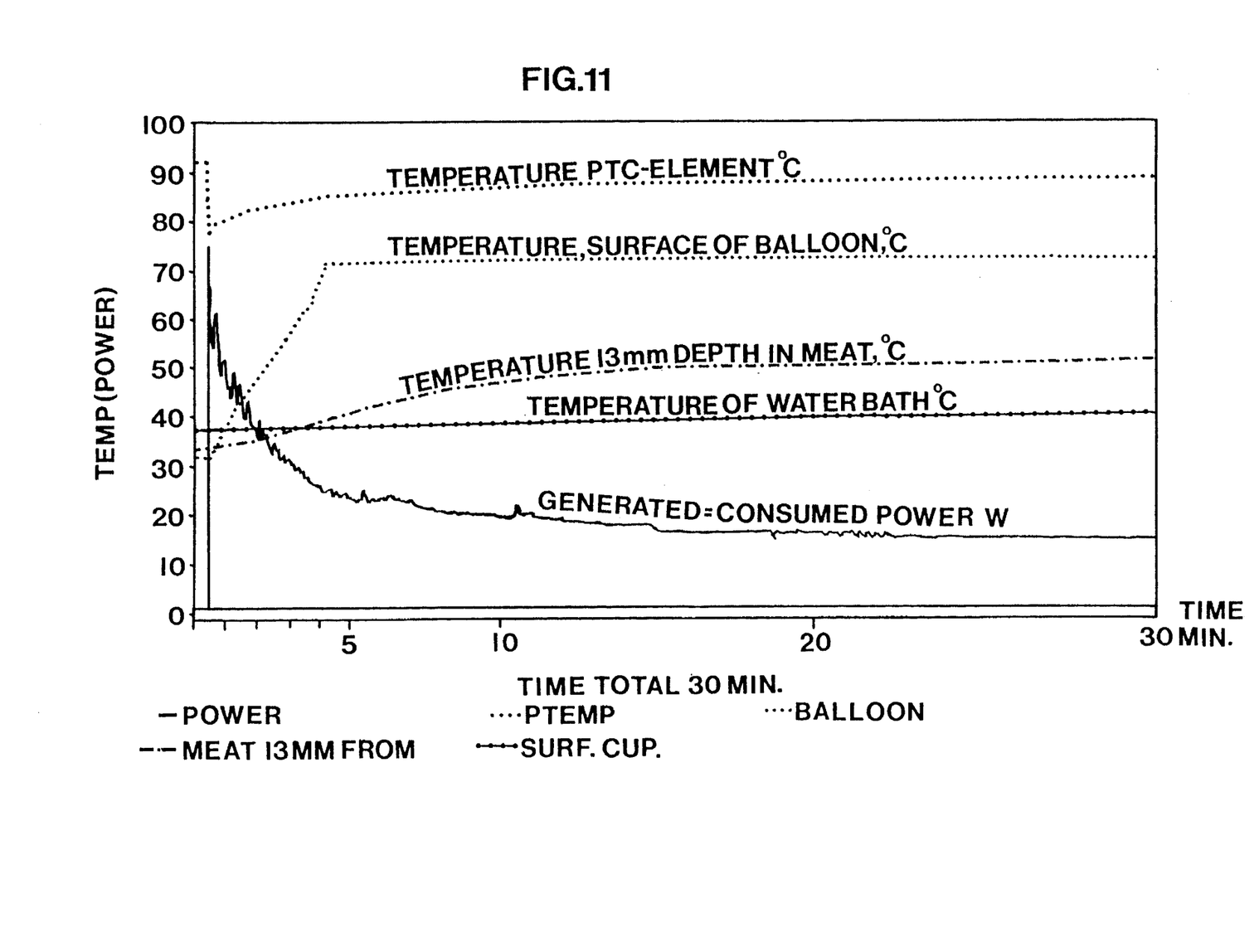
FIG. 11 shows a diagram on temperature/power as a function of time of treatment in connection with an experiment made.

FIG. 11 shows the results of in vitro experiments carried out on meat of beef. The experiments were performed by covering the inside of a thin-walled vessel having approximately the shape of a uterus on the inside with a layer of beef meat in a thickness of about 20–25 mm. The vessel was then placed in a water-bath having a temperature of 37° C. A catheter or instrument corresponding to that described in connection with FIG. 1 and with a central tube or body according to Type 1 of outer diameter 7 mm, generating 60 W as a start up maximum was inserted into the cavity within the meat, and the balloon was then expanded with a liquid consisting of an oxygen-free physiologic sodium chloride solution to a volume of 20 ml. A temperature sensor was place at a distance of about 13 mm within the meat counted from the wall of the expanding balloon. The voltage was then applied and the continued course of the experiment can easily be understood from the diagram shown in FIG. 11.

At the outset the temperature of the PTC-material immediately rose to above 90° C. without any generation of power. After half a minute the circulation pump was started and the power output immediately rose to 60–70 W at the same time as the temperature of the PTC-element decreased to 78° C. (Curie point 80° C.). Already after about 4 minutes the temperature at the surface of the balloon had increased to somewhat above 70° C. (treatment temperature), and the energy output had fallen to about 25 W. When continuing the experiment the temperature of the balloon surface remained constant, whereas the temperature 13 mm inside the meat slowly rose from 34° C. to about 50° C. after about 20 minutes, at the same time as the power output decreased to about 18 W. After about 5 minutes treatment conditions were reached. The treatment is then continued for say 30 to 40 minutes to give the desired result.

A voltage of 24 V was used in the experiments, but even lower voltages can be used in certain cases. Under all circumstances such low voltages are safe. In order to completely eliminate the risk for electro shocks the source of current is suitably for example a rechargeable battery.

As indicated the heat-emission from the PTC-elements is of decisive importance in order to obtain the highest possible power output, which will be obtained by an effective circulation of liquid which also has for a purpose to transfer the absorbed heat to the surface of the balloon and the surrounding tissue.

TABLE 1

|  | Type 1 | | | Type 2 | | | Type 3 | | | |
| --- | --- | --- | --- | --- | --- | --- | --- | --- | --- | --- |
| Outer diameter (mm) | 7 | 6 | 5 | 7 | 6 | 5 | 7 | 6 | 5 | 4 |
| Inner diameter (mm) | 6 | 5 | 4 | 6 | 5 | 4 | 5 | 4 | 3 | 2 |
| Power per cm length, W | 20 | 16 | 9.5 | 27 | 21 | 14 | 31 | 25 | 19 | 12,7 |

What is claimed is:

1. A device for carrying out hyperthermia in a body cavity or duct having a narrow access path, the device comprising:

an elongate distal section insertable into a body cavity or duct, the elongate distal section including a centrally located, heat-releasing element, which is either surrounded by an elongate housing or is itself constituted by an elongate housing;

means for supplying energy to the heat-releasing element;

an elastic enclosure surrounding said elongate housing in a fluid-tight manner;

wherein the elongate housing has an axially operating inlet passage at a proximal part of the housing adapted to communicate with a source of fluid and an outlet port opening to the elastic enclosure for supplying a heat-transmitting fluid under pressure from the housing to the elastic enclosure to accommodate and to exert a controlled pressure on walls of a cavity or duct in which the elongate housing is adapted to be inserted and which is adapted to surround the elongate housing; and means for circulating the fluid in a circuit between the housing and the elastic enclosure, wherein the housing has an inlet port to receive fluid from the elastic enclosure and the heat-releasing element is disposed between the inlet port and the outlet port;

at least one first back valve arranged in the inlet port to allow fluid into the housing from the elastic enclosure, the at least one back valve having a flow resistance in an open position that is lower than a flow resistance through the housing, wherein said means for circulating the fluid in a circuit provides a reciprocating movement of a small quantity of fluid enclosed in the inlet passage after expansion of the elastic enclosure, wherein fluid moves through the inlet into the housing to absorb heat from the heat-releasing element and from the outlet port into the elastic enclosure to release absorbed heat; and wherein the heat-releasing element is of an inherently self-regulating type and is selected from the group comprising a PCT semi-conductor material having a Curie temperature or Trip point, and a ferromagnetic material having a Curie point in combination with said means for the supply of energy being based on magnetic induction.

2. A device according to claim 1, wherein the device is configured for treatment of uterine disorders and the heat releasing element is of a semiconductor material and the material has a Trip or Curie point lying within the range about 60° C. to about 90° C.

3. A device according to claim 2, wherein the material has a Trip or Curie point lying within the range of about 70° C. to about 80° C.

4. A device according to claim 1, wherein the device is configured for treatment of prostatic disorders, and the material has a Trip or Curie point within a range about 45° C. to about 65° C.

5. A device according to claim 4, wherein said housing has an outer diameter of about 7–8 mm and has a flow capacity to release an amount of fluid to the elastic enclosure sufficient for a heat transfer of at least about 3 W/cm axial length of the housing at a predetermined treating temperature and at a voltage of 24 V.

6. A device according to claim 4 wherein the material has a Trip or Curie point within the range of about 48° C. to about 56° C.

7. A device according to claim 1, wherein the heat-releasing element comprises at least two axially and parallel arranged part-elements of a PTC semi-conductor material having substantially parallel surfaces, said part-elements being separated to form passages between and about the part-elements for a flow therethrough of the heat-transmitting fluid for effective and even heat-release to the heat-transmitting fluid.

8. A device according to claim 7, wherein the part-elements each have a thickness that is not greater than about 1.5 mm and that each part-element exhibits an energy generation at steady state of at least about 1 W/cm² exposed element surface at a voltage of about 24 V.

9. A device according to claim 1, wherein said means for internal circulation has a capacity at steady state conditions sufficient to exchange a fluid volume of the housing at a rate of at least about 30 fluid volume equivalents per minute.

10. A device according to claim 1, wherein said elongate housing comprises a cylindrical element formed of a PTC semi-conductor material having a central duct for a flow of the heat-transmitting fluid.

11. A device according to claim 1, wherein said at least one back valve comprises a flap valve.

12. A device according to claim 1, wherein said PTC material is shaped for a packing degree in a range of about 35 to about 70% by volume.

13. A device according to claim 1, wherein said heat-releasing element comprises a ferromagnetic material and the means for supplying energy to the heat-releasing element comprises an induction coil intended to surround a body part containing said body cavity or canal.

14. A device according to claim 13, wherein the ferromagnetic material is elongated in a direction of a magnetic induction field.

15. A device according to claim 14, wherein said ferromagnetic material is is shaped to have a packing degree lying within it range of about 25 to about 60% by volume.

16. A device according to claim 14, wherein said elongate distal section comprises a central tubular element and a plurality of parallel, longitudinally extending bars, bands or wires of a ferromagnetic material essentially evenly distributed around said central tubular element and constituting said means for heat generation.

17. A device according to claim 14, wherein said ferromagnetic material is selected from a group consisting of nickel and copper, nickel and silica, iron and platinum or iron and palladium.

18. A device according to claim 1, wherein the means for circulating the fluid comprises a reciprocating piston.

19. A device for carrying out hyperthermia in a body cavity or duct having a narrow access path, the device comprising:

an elongate distal section insertable into a body cavity or duct, the elongate distal section including a centrally located, heat-releasing element, which is either surrounded by an elongate housing or is itself constituted by an elongate housing;

means for supplying energy to the heat-releasing element;

an elastic enclosure surrounding said elongate housing in a fluid-tight manner;

wherein the elongate housing has an axially operating inlet passage at a proximal part of the housing to supply a heat-transmitting fluid under pressure to the housing and an outlet port opening to the elastic enclosure to supply the heat-transmitting fluid under pressure from the housing to the elastic enclosure for expansion of the elastic enclosure to accommodate and to exert a controlled pressure on walls of a cavity or duct in which the elongate housing is adapted to be inserted and adapted to surround the elongate housing; and means for circulating the fluid in a circuit between the housing and the elastic enclosure, wherein the housing has an inlet port to receive fluid from the elastic enclosure and the heat-releasing element is are disposed between the inlet port and the outlet port, at least one first back valve arranged in the outlet, a flow resistance of the inlet port being higher than a flow resistance through the housing, said means for circulating the fluid providing a reciprocating movement of a small quantity of the fluid enclosed in the inlet passage after expansion of the elastic enclosure, wherein fluid moves through the inlet port into the housing to absorb heat from the heat-releasing element and from the outlet port into the elastic enclosure to release absorbed heat; and wherein the heat-releasing element is of an inherently self-regulating type and is selected from the group comprising a PTC semi-conductor material of having a Curie temperature or Trip point, and a ferromagnetic material having a Curie point in combination with said means for the supply of energy being based on magnetic induction.

20. A device for carrying out hyperthermia in a body cavity or duct having a narrow access path, the device comprising:

an elongate distal section insertable into a body cavity or duct, the elongate distal section including a centrally located, heat-releasing element, which is either surrounded by an elongate housing or is itself constituted by an elongate housing;

means for supplying energy to the heat-releasing element;

an elastic enclosure surrounding said elongate housing in a fluid-tight manner;

wherein the elongate housing has an axially operating inlet passage at a proximal part of the housing to provide a heat-transmitting fluid under pressure to the housing and an outlet port opening to the elastic enclosure for supplying the heat-transmitting fluid from the housing to the elastic enclosure for expansion of the elastic enclosure to accommodate and to exert a controlled pressure on walls of a cavity or duct in which the elongate housing is adapted to be inserted and adapted to surround the elongate housing; and means for circulating the fluid in a circuit between the housing and the elastic enclosure, wherein the housing has an inlet port to receive fluid from the elastic enclosure and the heat-releasing element is disposed between the inlet port and the outlet port;

oppositely operating back valves arranged in the inlet port and the outlet port, wherein said means for circulating the fluid in a circuit provides a reciprocating movement of a small quantity of fluid enclosed in the inlet passage after expansion of the enclosure, wherein fluid moves through the inlet port into the housing to absorb heat from the heat-releasing element and from the outlet port into the elastic enclosure to release absorbed heat; and wherein the heat-releasing element is of an inherently self-regulating type and is selected from the group comprising a PCT semi-conductor material having a Curie temperature or Trip point, and a ferromagnetic material having a Curie point in combination with said means for the supply of energy being based on magnetic induction.

21. A device according to claim 20, wherein the device is configured for treatment of uterine disorders and the heat releasing element is of a semiconductor material and the material has a Trip or Curie point lying within a range about 60° C. to about 90° C.

22. A device according to claim 20, wherein the device is configured for treatment of prostatic disorders, and the material has a Trip or Curie point within a range about 45° C. to about 65° C.

23. A device according to claim 20, wherein the heat-releasing element comprises at least two axially and parallel arranged part-elements of PTC semiconductor material having substantially parallel surfaces, said part-elements being separated to form passages between and about the part-elements for a flow therethrough of the heat-transmitting fluid for effective and even heat-release to the heat-transmitting fluid.

24. A device according to claim 20, wherein said means for circulating the fluid has a capacity at steady state conditions sufficient to exchange a fluid volume of the housing at a rate of least about 30 fluid volume equivalents per minute.

25. A device according to claim 20, wherein said elongate housing comprises a cylindrical element formed of PTC semiconductor material having a central duct for a flow of the heat-transmitting fluid.

26. A device according to claim 20, wherein said means for circulating the fluid comprises one of a propeller and an axial pump wheel.

27. A device according to claim 20, wherein said means for circulating the fluid comprises a reciprocating piston having at least one axially directed aperture and at least one corresponding back valve, said piston providing axial flow of the fluid through said housing.

28. A device according to claim 20, wherein at least one of said back valves comprises a flap valve.

29. A device according to claim 20, wherein said PTC material is shaped for a packing degree in a range of about 35 to about 70% by volume.

30. A device for carrying out hyperthermia in a body cavity or duct having a narrow access path, the device comprising:

an elongate distal section insertable into a body cavity or duct, the elongate distal section including a centrally located, heat-releasing element, which is either surrounded by an elongate housing or is itself constituted by an elongate housing;

a flexible and elastic enclosure surrounding said elongate housing in a fluid-tight manner;

means for supplying energy to the heat-releasing element;

wherein the elongate housing has an axially operating first inlet passage at a proximal part of the housing and an outlet for supplying a heat-transmitting fluid under pressure from the housing to the elastic enclosure for expansion of the elastic enclosure to accommodate and to exert a controlled pressure on walls of a cavity or duct in which the elongate housing is adapted to be inserted surrounding the elongate housing;

wherein the elongate housing has an inlet port communicating with the elastic enclosure, the inlet port having a first back valve to allow flow into the housing only, the inlet port located on the housing so that the heat-releasing element is disposed between the inlet port and the outlet port;

a partition disposed in the housing between the heat-releasing element and one of the inlet port and the outlet port, the partition defining a chamber in the housing and having an axially directed aperture containing a second back valve which is oppositely acting relative to the first back valve placed in inlet port; and means for circulating the fluid through the housing, said means providing a reciprocating movement of a small quantity of the pressurized fluid enclosed in the inlet passage after expansion of the enclosure, so that the fluid flows from the housing to the elastic enclosure through the outlet port and returns to the housing through the inlet port; and wherein the heat-releasing element is of an inherently self-regulating type and comprises one of a PCT semiconductor material having a Curie temperature or Trip point, and a ferromagnetic material having a Curie point in combination with said means for the supply of energy being based on magnetic induction.

31. A device for carrying out hyperthermia in a body cavity or duct having a narrow access path, the device comprising:

an elongate distal section insertable into a body cavity or duct, the elongate distal section including a centrally located, heat-releasing element, which is either surrounded by an elongate housing or is itself constituted by an elongate housing;

an elastic enclosure surrounding said elongate housing in a fluid-tight manner; and means for supplying energy to the heat-releasing element;

wherein the elongate housing has an axially operating first inlet passage at a proximal part of the housing and an outlet port for supplying a heat-transmitting fluid under pressure from the housing to the elastic enclosure for expansion of the elastic enclosure to accommodate and to exert a controlled pressure on walls of a cavity or duct in which the elongate housing is adapted to be inserted surrounding the elongate housing;

wherein the elongate housing has an inlet port to receive fluid from the elastic enclosure, the inlet port located on the housing so that the heat-releasing element is disposed between the inlet port and the outlet port, means for circulation of said fluid through the housing and the elastic enclosure, said means located between the inlet port and the outlet port and providing an axial flow of the fluid through the housing, wherein the fluid moves through the housing past the heat-releasing element for absorbing heat from the heat-releasing element and from the outlet port into the elastic enclosure to release absorbed heat;

wherein the heat-releasing element is of an inherently self-regulating type and is selected from the group comprising a PCT semi-conductor material having a Curie temperature or Trip point, and a ferromagnetic material having a Curie point in combination with said means for the supply of energy being based on magnetic induction.

32. A device according to claim 31, wherein said means for circulating the fluid comprises one of a propeller and an axial pump wheel.

33. A device according to claim 31, wherein said means for circulating the fluid comprises a reciprocating piston having at least one axially directed aperture and at least corresponding back valve, said piston providing axial flow of the medium through said housing.

* * * * *